(12) United States Patent
Leung et al.

(10) Patent No.: US 9,381,518 B2
(45) Date of Patent: Jul. 5, 2016

(54) NANO-SUSPENSION PROCESS (71) Applicants: MERCK SHARP & DOHME CORP., Rahway, NJ (US); Dennis Leung, Rahway, NJ (US); Todd D. Nelson, Rahway, NJ (US); Timothy A. Rhodes, Rahway, NJ (US); Elizabeth Kwong, Kirkland (CA)

(72) Inventors: Dennis Leung, Scotch Plains, NJ (US); Todd D. Nelson, Creamridge, NJ (US); Timothy A. Rhodes, Wayne, PA (US); Elizabeth Kwong, Kirkland (CA)

(73) Assignee: Merck Sharp & Dohme Corp., Rahway, NJ (US)

( * ) Notice: Subject to any disclaimer, the term of this patent is extended or adjusted under 35 U.S.C. 154(b) by 171 days.

(21) Appl. No.: 14/354,187

(22) PCT Filed: Oct. 26, 2012

(86) PCT No.: PCT/US2012/062026
§ 371 (c)(1),
(2) Date: Apr. 25, 2014

(87) PCT Pub. No.: WO2013/066735
PCT Pub. Date: May 10, 2013

(65) Prior Publication Data
US 2014/0256818 A1 Sep. 11, 2014

Related U.S. Application Data (60) Provisional application No. 61/553,508, filed on Oct. 31, 2011.

(51) Int. Cl.
| | | |
|---|---|---|
| *A61K 9/14* | (2006.01) | |
| *B01F 11/00* | (2006.01) | |
| *B02C 19/18* | (2006.01) | |
| *A61K 9/10* | (2006.01) | |
| *A61K 9/16* | (2006.01) | |
| *A61K 31/192* | (2006.01) | |
| *A61K 47/10* | (2006.01) | |
| *A61K 47/26* | (2006.01) | |
| *A61K 47/32* | (2006.01) | |
| *A61K 47/38* | (2006.01) | |

(52) U.S. Cl.
CPC . *B02C 19/18* (2013.01); *A61K 9/10* (2013.01); *A61K 9/1688* (2013.01); *A61K 31/192* (2013.01); *A61K 9/145* (2013.01); *A61K 47/10* (2013.01); *A61K 47/26* (2013.01); *A61K 47/32* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 5,552,160 A * | 9/1996 | Liversidge | A61K 9/145 424/450 |
| 5,922,355 A | 7/1999 | Parikh et al. | |
| 7,188,993 B1 * | 3/2007 | Howe | B06B 1/161 366/111 |
| 2006/0003012 A9 | 1/2006 | Brynejlsen et al. | |
| 2006/0110462 A1 | 5/2006 | Papadopoulos et al. | |
| 2006/0134646 A1 | 6/2006 | Ansari et al. | |
| 2006/0141048 A1 | 6/2006 | Kipp et al. | |
| 2006/0198893 A1 | 9/2006 | Lindfors et al. | |
| 2007/0108320 A1 | 5/2007 | Pfeffer et al. | |
| 2008/0033296 A1 | 2/2008 | Isern et al. | |
| 2008/0251375 A1 | 10/2008 | Hielscher et al. | |
| 2010/0310661 A1 | 12/2010 | Chen et al. | |
| 2011/0223216 A1 | 9/2011 | Da Rocha et al. | |

FOREIGN PATENT DOCUMENTS

| | | |
|---|---|---|
| WO | WO0004978 | 2/2000 |

OTHER PUBLICATIONS

Product Spec Sheet for Resodyn LabRAM (2015); www.resodynmixers.com/products/labram/.*
International Search Report for PCT/US12/62026 dated Oct. 26, 2012.

* cited by examiner

*Primary Examiner* — Jeffrey T Palenik
(74) *Attorney, Agent, or Firm* — H. Eric Fischer; John C. Todaro (57) ABSTRACT

Described herein is a process for preparing nano-suspensions, wherein the process comprises: providing an admixture of at least one active pharmaceutical compound, an aqueous dispersion medium, and milling media and applying thereto acoustic energy having a frequency of from about 10 hertz to 1000 hertz and which supplies a linear acceleration of from about 10 G's to about 100 G's (where "G" is the force of gravity) for a period sufficient to supply a nano-suspension having a $D_{50}$ of less than about 1 micron, preferably less than about 500 nm. Described also are nano-suspensions having novel properties prepared via the inventive process.

14 Claims, 5 Drawing Sheets

NANO-SUSPENSION PROCESS

CROSS REFERENCE TO RELATED APPLICATIONS

This application is a U.S. National Phase application under 35 U.S.C. §371 of PCT Application No. PCT/US2012/062026, filed Oct. 26, 2012, which claims priority under 35 U.S.C. §119(e) from US Ser. No. 61/553,508, filed Oct. 31, 2011.

BACKGROUND OF THE INVENTION

Nano-suspensions are emerging as a preferential form of active pharmaceutical compounds which are BCS class II and class IV (aqueous insoluble) drug substances in the provision of oral and injectable medicaments comprising such compounds. Reviews highlighting the possibilities of this approach in the provision of medicaments include: Critical Reviews in articles by Bala, I. et al. in *PLGA Nanoparticles in Drug Delivery: State of the Art*, Therapeutic Drug Carrier Systems, 2004, Vol 21, issue 5; Rabinow, B. E. in *Nanosuspensions in Drug Delivery*, Nature Reviews, Drug Discovery, Vol 3 (2004) pp 785-796; Patravale, V. B. et al. in *Nanosuspensions: a promising drug delivery strategy*, Journal of Pharmacy and Pharmacology, (2004) 56: pp 827-840; and Koteshwara, K. B. et al. in *Nanosuspensions: a Novel Drug Delivery Approach*, Int. Journal. Of Res. In Ayurveda & Pharmacy, (2011), 2(1) pp 162-165. When utilized in medicaments for oral administration, nano-suspensions of class II and class IV drug substances can provide a dosage form which addresses the twin problems of low solubility and poor bioavailability by providing these compounds in a form in which the very small particle size presents an extremely large surface area of the compound to the biosystem to which it is administered, reducing bathers to dissolution and absorption. When utilized in medicaments for administration via injection, nano-suspensions can provide a dosage form which contains high drug loading and is readily dispersed within the system into which it is injected.

Typically, nano-suspensions of active pharmaceutical compounds are prepared by application of extremely high shear conditions to a mixture of the compound, an aqueous dispersion medium, and milling media (herein, "high-shear milling"). In most high-shear milling applications the milling media is a small polyester prill driven by the shear forces to which it is subjected, and acts like a microscopic ball mill, impacting the pharmaceutical compound present in the mixture (generally, the active pharmaceutical compound (APC) is present in the slurry initially as a powder, in the form of a macroscopic particulate, with $D_{50}$ in excess of one micron). Typical equipment employed in preparing such nano-suspensions is a high-shear mixer in which a stainless steel impeller rotates at multiple thousand RPM in a chamber holding a mixture of the active pharmaceutical compound, aqueous dispersion medium, and milling media. An example of commercially available equipment utilized in this process is the Elan Nanomill®.

There have been reports of difficulties presented in the provision of nano-suspensions using a high-shear mixing process, for example, shedding of metal particles as a result of the high-shear stresses imposed on the equipment used in preparing the nano-suspension, heating of the admixture from which the nano-suspension is prepared, resulting in degradation of drug product, limitations on drug loading, and long periods of mixing required to prepare nano-suspensions mitigate against using such a process for providing commercial quantities of a nano-suspension of an APC for use in commercial preparation of medicaments. In addition to these drawbacks, scaling high-shear milling equipment and processes from "bench-scale" preparation of a nano-suspension to a commercial scale requires extensive engineering and process development. The need for a mixing and recirculating chamber imposed by the high-shear process requirements presents special difficulties in adopting such processes for aseptic manufacturing. The ability to compare various formulations in the development of a nano-suspension as an active pharmaceutical ingredient for commercial scale production of medicaments also presents difficulties such as equipment-limited throughput of screening formulations and the difficulties in maintaining consistent conditions across multiple runs using different formulations.

In view of the foregoing, there is a need for improving the process by which nano-suspensions are prepared.

Acoustic mixers, for example, the Resodyn™ acoustic mixer, are commercially available. This technology has been described, for example, in U.S. Pat. No. 7,188,993 to Howe et al., and employs linear displacement to introduce a standing linear acoustic wave into a medium, for example, gas, liquid or solid, residing within a container affixed to the device. Preparation of admixtures comprising energetic or shock-sensitive materials has been described using acoustic mixing, for example, in Published U.S. Patent Application 2010/0294113 (McPherson). Suspension of pre-formed nanoparticulate materials in an aqueous medium has also been described, for example, the dispersion of silver nanoparticles of 20 nm-30 nm in water using an acoustic mixer (Resodyn™ marketing literature)

SUMMARY OF THE INVENTION

The process of the present invention addresses the above-mentioned unmet needs present in high-shear processes for the preparation of nano-suspensions, and provides other advantages that will become apparent from the following. Thus, in one aspect the present invention is a process for preparing a nano-suspension from an active pharmaceutical compound comprising: (i) providing an admixture of at least one active pharmaceutical compound, an aqueous dispersion medium, and milling media; and (ii) applying acoustic energy having a frequency of from about 10 hertz to 1000 hertz to said admixture, wherein preferably the acoustic energy is a standing wave supplying a linear acceleration of from about 10 G's to about 100 G's (where "G" is the force of gravity), for a period sufficient to form a nano-suspension having a particle $D_{50}$ of less than about 1 micron, preferably a particle $D_{50}$ of less than about 500 nm.

Typically, the nano-suspension thus provided is separated from the milling media, preferably by decanting or by centrifuging over a sieve sized appropriately to separate the milling media from the nano-suspension. Once a nano-suspension has been recovered in this manner, optionally, the aqueous dispersion medium can be removed, for example by lyophilization, to obtain nanoparticles of the active pharmaceutical compound in the solid state.

In one aspect the present invention is a nano-suspension made in accordance with the process of the present invention, preferably a nano-suspension comprising at least one BCS class II or class IV active pharmaceutical compound. In some embodiments it is preferred to provide a nano-suspension wherein said suspension comprising nanoparticles of active pharmaceutical compound (APC) with in excess of about 95 wt. % APC loading.

BRIEF DESCRIPTION OF THE DRAWINGS

The present invention is more fully described in the following detailed description and the appended figures in which.

DETAILED DESCRIPTION OF THE INVENTION

The process of the invention comprises admixing in a slurry-container an aqueous dispersion medium, at least one active pharmaceutical compound, and milling media, and subjecting the admixture to acoustic energy of sufficient frequency and amplitude, and for a sufficiently sustained period, to provide a nanoparticle suspension (nano-suspension) of the APC dispersed in the aqueous dispersion medium. In nano-suspensions of the invention, after the nano-suspension has been milled to the desired particle size the nano-suspension is separated from the milling media. As will be appreciated, recovery of the nano-suspension (separation from the milling media) can be accomplished by any known physical separation method, for example, where the media permits, separation can be accomplished by decantation, for example, as in the case of the Examples of the invention presented herein, a nano-suspension prepared using YTZ milling media can be recovered using a 20 gage needle and syringe since the milling media is of sufficient density and size to permit such separation. Where decantation is not possible, for example where the milling media is polyester prill, size exclusion separation can be employed, for example, by centrifuging through a properly sized sieve.

As the term is used herein, acoustic energy is linear or spherical energy propagation through a tangible medium which is within the frequency range of 10 hertz to 20,000 hertz. In some embodiments of the process of the present invention, it is preferred to employ linear acoustic energy at a frequency of from about 10 hertz up to about 100 hertz, more preferably the acoustic energy is supplied at a frequency of about 60 hertz. It will be appreciated that in processes of the invention, in accordance with known principles, the exact frequency will be selected to provide a standing wave in the slurry from which a nano-suspension is being provided. The frequency required to achieve a standing wave will vary according to known principles depending upon the nature of the slurry and the dimensions of the slurry to which acoustic energy is applied.

Acoustic energy can be supplied to an admixture using any known source, however, in general it is preferred to supply the energy by cyclic linear displacement of a container filled with the admixture. In processes of the invention, preferably the acoustic energy supplied by linear displacement exerts between about 10 times G-force (where "G" is the force of gravity) and about 100 times G-force. Although it will be appreciated that numerous mechanical or electronic transducer arrangements can be utilized to supply the cyclic linear displacement required to generate the desired G-force within the desired frequency range, one example of commercially available equipment suitable for supplying the necessary acoustic energy is the Resodyn™ acoustic mixer (Resodyn Acoustic Mixers, Inc.), which makes equipment available in a range of capacities from bench-scale to multi-kilogram capacity.

As mentioned above, it was previously known that an acoustic mixer such as a Resodyn™ acoustic mixer could be used to efficiently provide suspensions by mixing pre-formed nano-particulate materials and an aqueous dispersion medium, however, acoustic mixing has not been previously employed to prepare nanoparticles from bulk powdered solid materials (i.e. macro-particulate materials defined herein as having a $D_{50}>1$ micron). Surprisingly, the inventors have found that the use of acoustic energy to prepare a nano-suspension from macro-particulate solid materials provides a nano-suspension product which has unique stability and unique properties not available in a nano-suspension prepared using high-shear mixing. Example of such properties provided by nano-suspensions prepared in accordance with the process of the present invention include: (i) nano-suspensions exhibiting higher loading of active pharmaceutical compound; (ii) nano-suspensions exhibiting reduced amounts of agglomeration; and (iii) nano-suspensions exhibiting reduced amounts of degradation products from the APC used in the admixture from which the nano-suspension was prepared.

Without wanting to be bound by theory, it is believed that supplying a standing wave of acoustic energy to the admixture used in preparing a nano-suspension in accordance with the process of the present invention provides uniform distribution of the energy supplied throughout the admixture, and consumes a smaller percentage of the energy supplied in shear heating of the admixture. This has the measurable advantages that nano-particulation occurs more efficiently, thus particles of a particular $D_{50}$ are provided in a shorter period of time. Moreover, and again, not being bound by theory, it is believed that because acoustic milling directs less energy to shear and translational forces during nano-particulation, the admixture undergoes less heating during the milling process, and the metal particle shedding, which is common in processes utilizing shear forces to mill particles, is reduced or eliminated when acoustic energy is employed. Again, not wanting to be bound by theory, it is believed that the uniform distribution of energy within the admixture during nano-particulation results in lower energy being imparted to the macro-particulate APC solid present in the slurry as it is being milled, resulting in less surface energy needing to be dissipated in the nanoparticles produced, leading to a more stable nano-suspension and permitting higher ratios of (pharmaceutical compound)/(suspending media), affording a nano-suspension which has higher loadings of active pharmaceutical compound per unit volume relative to the surface-active constituents employed.

This system has been modeled to try and further illustrate and contrast the forces involved in traditional high-shear milling and acoustic milling used in preparing the nanosuspensions of the present invention. The magnitude and distribution of shear stresses within a tradition impeller agitated mill and an acoustic mill are different due to differences in the way energy is imparted to the fluid in each system. The shear stress ($\tau$) can be calculated, as shown below, as the viscosity of the fluid ($\mu$) multiplied by the shear rate ($\gamma$), where the shear rate is equivalent to the velocity gradient ($\nabla v$) within the flow field.

$$\text{shear stress} = \tau = \mu\gamma = \mu\nabla v$$

Since fluid and particle motion within the acoustic system is driven by the motion of the entire grinding chamber, the velocity gradient (and therefore the distribution of shear stress) is expected to be more uniform as compared with the impeller system where high velocity gradients exist. Uniform distribution of stresses allows for more efficient use of energy during milling. For the impeller driven system, higher shear conditions are needed to ensure energy is propagated from the centrally located impeller through the grinding volume for particle milling to proceed. Without wanting to be bound by theory it is believed that this less effective use of energy exposes particles and the grinding media to highly non-uniform stresses leading to undesirable results, for example, API degradation and metals shedding.

When an impeller is employed to impart energy to the milling operation, the stresses imparted to the slurry by the impeller are believed not only to be less uniform but also to have regions of higher magnitude than are experienced within a mixture where milling is driven by acoustic energy due higher local velocity gradients. When fluid motion is driven by the impeller imparting energy, fluid elements that are in direct contact with the impeller experience a velocity maximum in the region local to the impeller and velocity rapidly decreases to zero at the stationary outer walls of the grinding chamber. In systems where fluid motion is driven by acoustic energy, motion is imparted substantially uniformly throughout all volume elements of the grinding chamber providing lower velocity gradients within the material in the grinding chamber. Accordingly, energy is imparted more uniformly across the fluid which is believed to distribute stress more uniformly throughout the material in the chamber and impart lower overall magnitude of shear stress.

The maximum velocity of an impeller driving the grinding process can be defined by the tip speed of the impeller, which can be calculated as shown in the equation below, $$\text{tip speed} = v_{tip} = 2\pi\omega r,$$

where, $\omega$ and $r$ are the angular velocity and radius of the impeller respectively. At the typical operating conditions applied during milling (14.5 mm radius impeller rotating at ~4280 rpm), tip speeds are on the order of 6.5 m/s and remain constant throughout processing.

For a milling operation driven by acoustic energy, the motion of the grinding chamber is confined to the vertical direction (z) and can be described by the set of equations below, $$\text{position} = z = a\sin(\omega t)$$
$$\text{velocity} = \frac{dz}{dt} = a\omega\cos(\omega t)$$
$$\text{acceleration} = \frac{d^2 z}{dt^2} = a\omega^2\sin(\omega t)$$

where, a and $\omega$ are the amplitude and frequency of vibration (~3 mm and ~60 htz) respectively.

Figure 4:
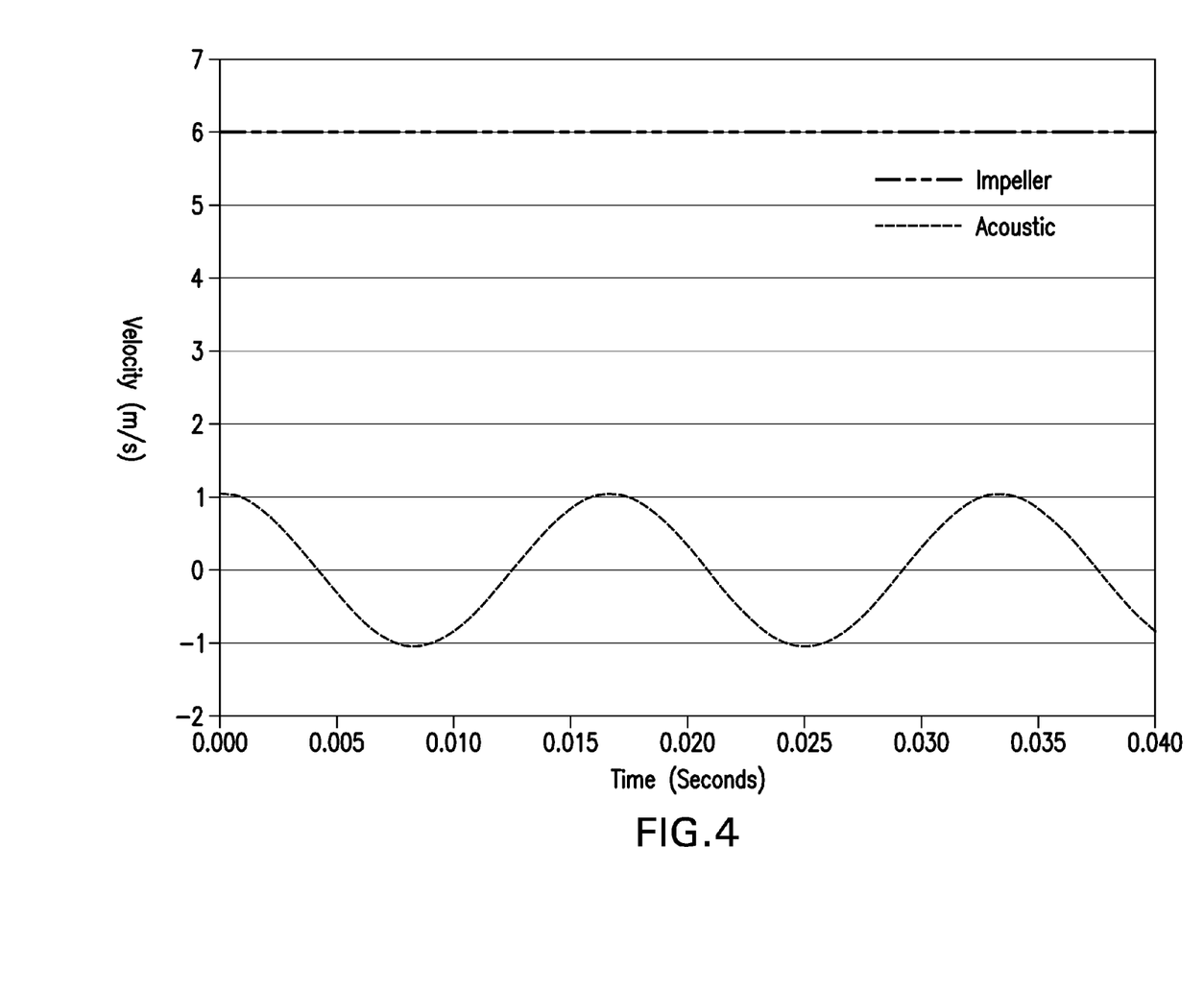
FIG. 4 presents a graphic comparison of shear observed within an acoustically-driven milling system and a conventional stirred milling system.

For typical operating conditions of 40 to 50 times the acceleration of gravity, the maximum velocity of the chamber is on the order of 1 m/s. The velocity varies as a function of time according to the equation above and is at least 6.5 times less then the speeds of a typical impeller agitated system. This difference in velocity between the two methods of milling is presented graphically in FIG. 4 where the maximum velocities observed in an impeller-driven milling operation and in an acoustic energy-driven milling operation have been plotted for comparison. It is this difference that is believed to lead to differences in the milling performance of observed for each system.

Figure 5A:
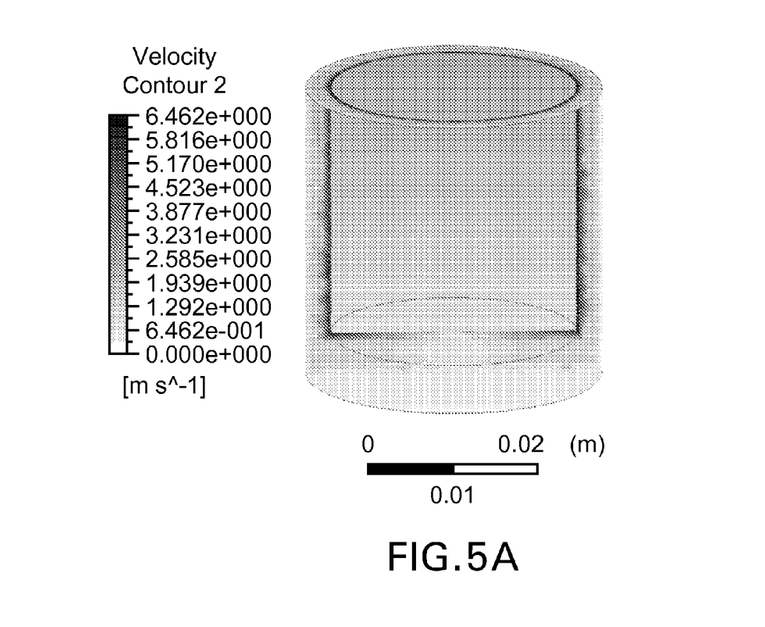
FIG. 5 presents different sectional views depicting the shear forces within an impeller-driven milling system as a function of distance from the impeller.
Figure 5B:
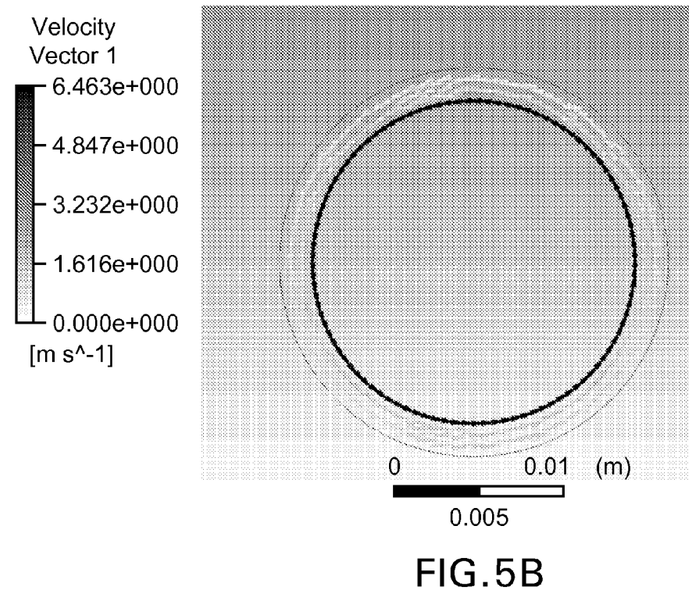

FIG. 5 presents steady state (time independent) velocity profiles which were generated for an impeller agitated system by performing computational fluid dynamics (CFD) simulations using ANSYS Fluent software. The system was modeled as a smaller cylinder rotating in a stationary larger cylinder with geometric dimension similar to the actual mill. Water was used of the system fluid. These results are presented in FIG. 5a, which illustrates the velocity gradient within a vertical slice through the mill and the upper surface of the vessel while FIG. 5b presents a close-up of the velocity profile at the upper surface of the vessel. The empty region in the center of the figures represents the rotating impeller while fluid regions are shaded according to velocity magnitude with dark gray being the highest values (max ~6.5 m/s) and light-gray to white being the lowest values.

These data graphically presented in FIG. 5 show that a relatively high velocity gradient exists within the impeller-driven milling system (very small area of dark gray surrounded by a region which is lighter gray shading). Velocity within the system decreases rapidly from the high-velocity region in the center, near the impeller, moving toward the outer walls of the chamber. This large velocity gradient leads to relatively high shear stresses and the attendant problems described above.

As the term is used herein, a nano-suspension comprises sub-micron particles (i.e., particles yielding a $D_{50}$ measurement of <1 micron) of an active pharmaceutical compound (APC, i.e. drug substance) present as a colloidal dispersion in an aqueous dispersion medium. In general, the APC present in a nano-suspension of the present invention comprises an active pharmaceutical compound of low aqueous solubility (for example, a BCS (Biopharmaceutical Classification System) Class II or Class IV drug substance), and is preferably a BCS Class IV drug substance. The term "macro-particulate" material is used herein to distinguish nano-particulated materials provided by the process of the present invention from powdered material provided by ordinary milling or precipitation techniques, for example, those typically used to provide a bulk solid active pharmaceutical compound, and which in general have a $D_{50}$ value well in excess of 1 micron.

In general, the aqueous dispersion medium employed in nano-suspensions of the invention comprises primarily water (based on wt. %) and one or more water-miscible surface-active constituents. In nano-suspensions of the present invention, preferably the surface-active constituents are water-miscible polymers, described in detail herein, and optionally, comprises also a surfactant. When a surfactant is employed in aqueous dispersions medium used to prepare a nano-suspension of the invention, preferably the surfactant is an ionic surfactant, described in detail herein.

It will be appreciated that two important metrics of a nano-suspension are: (i) the ratio of drug to aqueous dispersion medium which can be employed in a slurry from which the nano-suspension is prepared; and (ii) the ratio of APC to the surface active constituents (water-miscible polymer and optional surfactant) employed in the slurry from which the nano-suspension is prepared to stabilize the nanoparticles formed. As will be understood from the Examples which follow, the process of the present invention permits preparation of nano-suspensions in which the slurry can employ a higher weight percentage (wt. %) of the APC relative to the aqueous dispersion medium (water and surface-active constituents described above). Moreover, again with reference to the Examples which follow, the process of the present invention permits nano-suspensions to be prepared wherein the nanoparticles in the suspension comprise a greater wt. % of APC relative to surface-active constituents present than is available using high-shear processing. This in turn permits nano-suspensions of the invention to exhibit higher APC loadings than are available from previous processes.

As mentioned above, an aqueous dispersion medium utilized in a nano-suspension of the present invention comprises water and one or more surface-active constituents which stabilize the particles present in a nano-suspension. Although the ratio of aqueous dispersion medium and APC will vary depending upon the nature of the APC, in general the slurry from which a nano-suspension is prepared will comprise from about 1 wt. % APC relative to the weight of the aqueous dispersion medium employed up to about 40 wt. % relative to the weight of aqueous dispersion medium employed.

With regard to the wt. % ratio of APC to surface-active constituents present in the aqueous dispersion medium (and therefore associated with the nanoparticles present in a nano-suspension of the invention at the conclusion of the milling process), the ratio will vary depending upon the nature of the APC employed. In general it is preferred to prepare a nano-suspension with the highest weight ratio of APC relative to the weight of surface-active constituent which will provide a stable nano-suspension. In some embodiments it is preferred to provide nano-suspensions of the invention comprising from about 25 wt. % to about 99 wt. % APC relative to the weight of surface-active constituents present in the nano-suspension. In some embodiments it is preferred to provide nano-suspensions having in excess of at least about 40 wt. % APC relative to the weight of surface-active constituents present in the nano-suspension. In some embodiments it is preferred provide nano-suspensions having more than 90 wt. % APC relative to the weight of surface-active constituents employed and in some embodiments more than 95 wt. % APC relative to the amount of surface-active constituents employed. In some embodiments, as much as 98 wt. % APC is present relative to the amount of surface-active constituents employed.

In general, surface-active polymers suitable for use in the present invention are water miscible polymers. Examples of suitable polymers include, but are not limited to: polymers based on hydroxypropylcellulose, for example, HPC-SL (Ashland Chemical); alkoxide block copolymers, for example an ethylene oxide/propylene oxide copolymer, for example, Plurionic F127 from BASF; polyethylenesorbitol polymers, for example Tween 80 (Sigma, article of commerce); polyvinylpyrrolidone polymers, for example, Plasdone® from Ashland Chemical; Methyl Cellulose (article of commerce, for example, available from Sigma) and cellulose derivatives, for example, carboxycellulose derivatives, for example, hydroxypropylmethyl cellulose derivatives, for example, Methocel polymers from Dow Chemical, and polypropylene- and polyethylene glycol polymers and derivatives, for example, Carbowax® available from Dow Chemical. It will be appreciated that other surface-active polymers may be employed, dictated by the nature of the active pharmaceutical compound being dispersed.

In some embodiments, the surface-active polymer is combined with a surfactant to help maintain dispersion. As is known, the nature and amount of surfactant employed will depend upon the polymer employed and the nature of the surface of the particles of active pharmaceutical compound dispersed. Examples of surfactants suitable for use in nano-suspensions of the present invention include, but are not limited to, dioctyl sulfosuccinates (docusate sodium, DOSS, article of commerce), and sodium dodecylsulfate, an ionic surfactant prepared from laurel alcohol, an article of commerce, both available, for example, from Fluka.

As mentioned above, a nano-suspension of the invention is prepared by applying acoustic energy to a slurry contained in a suitable slurry container. For carrying out the process of the invention, any convenient, sealable container may be employed which can be fixed to the carriage of the acoustic mixing equipment utilized to prepare the slurry. Examples of suitable containers are, but not limited to, sealable bottles (of any material, for example, glass, plastic or metal, preferably glass or plastic), a sealable plastic bag, and a sealable microtiter well plate.

It will be appreciated from the foregoing that the flexibility of choice in suitable slurry container means that the process of the present invention readily affords the ability to provide nano-suspensions under aseptic manufacturing conditions as well as provides "line-of-sight" scalability of a particular set of parameters from "bench-scale" batch size to volumes suitable for commercial preparation of nano-suspension in the provision of an API on a commercial scale.

In one aspect the present invention is a nano-suspension prepared by the process of the invention. As mentioned above, and exemplified below, nano-suspensions prepared by the process of the invention exhibit lower levels of degradation products and metal loading, and can exhibit higher APC loadings than nano-suspensions prepared by high-shear milling processes from comparably constituted slurries. For example, using the process of the present invention, nanoparticles having APC loadings of greater than 90 wt. % can be prepared, which are not available using high-shear milling processes. Moreover, it will be appreciated that the process of the present invention is readily adaptable to either a "batch" or "continuous process" mode for large-scale preparation of nano-suspensions for use in the preparation of medicaments.

It will be appreciated that the process of the present invention is amenable to the provision of multiple simultaneously-prepared samples of a nano-suspension using the same mixing conditions. This latter feature permits variations of a formulation to be prepared simultaneously, under the same conditions, for the purposes of comparing or optimizing formulations. It will be appreciated that this aspect of the present invention provides for the screening and optimization of formulations while consuming only small amounts of APC when a small sample size is prepared, for example, by the use of a sealable micro-titer well plate as a slurry container.

The present invention will be further understood from the following examples, which are meant to illustrate rather than limit the invention.

EXAMPLES

The following examples demonstrate the advantages available from the process of the present invention and the superior nano-suspensions provided according to the present invention.

In the following examples, nano-suspensions of the invention were prepared in cells fabricated in house with acoustic power supplied using a Resodyn™ Resonant Acoustic Mixer® (LabRAM™) and the indicated power settings. In the examples, comparative nano-suspension samples were prepared using an Elan Nanomill® apparatus (available from Elan Delivery Systems, Alkermes plc, Nanomill-01®) equipped with a 10 mL stainless steel mixing chamber and mixing probe.

Example nano-suspensions were evaluated for particle size and particle size distribution using dynamic light scattering (DLS, Wyatt, DyanoPro Plate Reader). Results reported for particle size analysis ($D_{50}$ and $D_{90}$) have their ordinary meaning as understood in the art of particle-size analysis. Unless otherwise indicated, values for $D_{50}$ and $D_{90}$ are reported in nanometers (nm). The APC in example nano-suspensions was evaluated using high performance liquid chromatography (HPLC, Hewlett Packard, Agilent 1100). Residual metals analysis was performed using inductively coupled plasma mass spectroscopy (ICP-MS, Perkin Elmer).

As used in the examples, all reagents are articles of commerce unless otherwise noted. Pluronic F127 is an ethylene oxide/propylene oxide copolymer, article of commerce, for example, available from BASF, HPC-SL is SL-grade hydroxypropylcellulose, available from Ashland Chemical, Tween 80 is a polyethylenesorbitol product available from Sigma, SDS is sodiumdodecylsulfate (article of commerce), DCA is sodium deoxycholate (article of commerce), PVP is polyvinylpyrrolidone (Article of commerce, for example, Plasdone® from Ashland Chemical), HPMC is hydroxypropylmethylcellulose, an article of commerce.

Example 1

Comparison of Nano-Suspensions Prepared From Comparable Slurries Using High-Shear Milling (Prior Process) and Acoustic Milling (Process of the Invention)

In a direct comparison between the provision of a nano-suspension via milling with high-shear mechanical stirring and milling using low frequency acoustic mixing, a 10 mL milling chamber (for use in a Nanomill® high-shear mechanical milling machine) and an 8 mL capped glass vial (for use in a Resodyn™ LabRAM™ acoustic mixer) were charged with the mixture shown, in the amounts shown in the respective columns of Table I labeled for the Nanomill® or Acoustic Mixer. Thus charged, the 10 mL milling chamber and 8 mL capped glass vial were fitted, respectively, into the Nanomill® and the LabRAM™ acoustic mixer and each apparatus was operated for 90 minutes. The resulting material was evaluated and the results presented in Table II, below.

TABLE I

| Constituent | Weight charged Nanomill® 10 mL milling chamber | Weight Charged into 8 mL glass vial (Acoustic Mixer) |
|---|---|---|
| Naproxen sodium (USP) | 233 mg | 176 mg |
| Milling media | 5.43 g polystyrene milling beads (Elan Drug Technologies) | 9.12 g yttria-stabilized zirconia milling beads (Tosoh YTZ(R) grinding media) |
| Aqueous 5% PVP-K29-32 polymer dispersion medium | 1.165 g | 0.876 g |
| Aqueous 5% SDS surfactant | 0.093 g | 0.036 g |
| Water | 3.169 g | 2.272 g |

TABLE II

| Property | Elan Nanomill® | Resodyn™ LabRAM™ |
|---|---|---|
| Sample Temperature at end of milling period | 52° C. | 26° C. |
| Drug nanoparticle diameter ($D_{50}$) | 354 nm | 286 nm |
| Residual Metals | >1000 ppm | <1 ppm |
| Yield, wt. % (weight drug recovered/weight drug employed) | 56% | 84% |

The temperature of each nano-suspension was determined using a thermometer immediately after the milling time was completed. Particle size and metals content were analyzed as described herein. The nano-suspension product produced in each operation was recovered through centrifuge filtration over a 10 micron polypropylene mesh (Nanomill) or through a syringe equipped with a 20-gauge needle (acoustic mixer). In the case of the nano-suspension prepared with acoustic mixing, the YTZ milling media is sufficiently dense that it settles from the nano-suspension and permits separation by decantation without the need for separation through a mesh.

Comparative Example 2

Preparation of Nanoparticles Using a High-Shear Mechanical Milling Apparatus (10-mL Scale)

Nano-suspensions were made using conventional high-shear milling equipment (Nanomill®), an APC and an aqueous dispersion medium comprising water, a surface active polymer and in some cases a surfactant. For use in preparing these suspensions, an aqueous solution of surface-active polymer was prepared by dissolving 50 g of the selected polymer in 950 mL water (5 wt. % polymer solution). Where a surfactant was employed, a stock 5 wt. % aqueous solution of surfactant was prepared by dissolving 50 g of sodium dodecyl sulfate in 950 mL water for addition to the aqueous dispersion medium, as required.

In a typical run, a Nanomill® milling chamber of 10 mL volume was charged with 5.43 g of cross-linked polystyrene milling beads (Elan Drug Technologies), into which was added 0.233 g of "Test APC A" (a class IV drug substance), 1.165 g of the suspending polymer aqueous solution (5 wt. % suspending polymer in water) and (when employed as indicated in Table III) 0.093 g of the aqueous 5% surfactant solution. The admixture was blended by hand using a spatula, then the mixing chamber was fitted to the Nanomill® apparatus and the impeller operated at 5500 rpm for 90 minutes. The resulting suspension was centrifuge filtered over a 10 micron polypropylene filter and the recovered nano-suspension thus obtained was subjected to particle size analysis using the above-described procedure. The results (both for $D_{50}$ and $D_{90}$) are reported in Table III for several different combinations of APC and aqueous dispersion medium.

TABLE III

| No. | Suspending Polymer (5 Wt. % aqueous solution) | Surfactant (5 Wt. % aqueous solution) | Particle Diameter $D_{50}$ nm/$D_{90}$ nm |
|---|---|---|---|
| S-1 | Pluronic F127 | None | 214 nm/290 nm |
| S-2 | PVP K29-32 | SDS | 880 nm/1636 nm |
| S-3 | Tween80® | None | 1340 nm/2070 nm |

These data indicate that for "Test APC A", using high-shear milling to prepare a nano-suspension, a stable nano-suspension was only provided using Pluronic polymer in the aqueous dispersion medium, while significant agglomeration was observed for the samples using other polymers and surfactant.

Example 3

Preparation of Nano-Suspensions of "Test APC A" Using Acoustic Mixing (0.35-mL Scale)

A 5 wt. % aqueous solution of the selected polymer was prepared by dissolving 50 g of the selected polymer 950 g of water. In the same manner, a 1 wt. % aqueous solution of surfactant was prepared by dissolving 10 g of the selected surfactant with 990 g of water. These solutions were employed as prepared in providing nano-suspensions according to the invention.

Each well of a 350 µL plastic 96-well microtiter plate was charged with 0.80 g of yttria-stabilized zirconia milling beads (Tosoh YTZ® Grinding Media) and 4 mg of "Test APC A" (a class IV drug substance used in Example 2). Into this mixture was added 19 µL of a 5% aqueous solution of polymer (see Table IV) and, where employed, 4 µL of a 1% aqueous solution of surfactant (see Table IV) and 123 µL of water. Thus charged, the microtiter plate was thermally sealed and placed into the acoustic mixer (Resodyne™ LabRAM™). The acoustic mixer was operated at 60 Hertz, 40% power for 90 minutes. The resulting nano-suspension was separated from the milling media and recovered using a syringe equipped with a 20-gauge needle and the nano-suspension thus obtained was evaluated. Particle size analysis was performed in accordance with the description above and the results are reported in Table IV, below.

TABLE IV

| No. | Suspending Polymer | Surfactant | Particle Diameter $D_{50}$ nm/$D_{90}$ nm |
|---|---|---|---|
| A-1 | Pluronic F127 | None | 260 nm/406 nm |
| A-2 | PVP K29-32 | SDS | 238 nm/264 nm |
| A-3 | Tween80 ® | None | 342 nm/556 nm |
| A-4 | HPC-SL | SDS | 268 nm/342 nm |
| A-5 | HPMC | SDS | 240 nm/256 nm |

These data indicate that a stable nano-suspension could be prepared using "Test APC A" for all of the polymer and surfactant combinations tested in Comparative Example 2. Comparison of these data to the results reported in Comparative Example 2 (nano-suspensions prepared via high-shear milling utilizing the same constituents in the same ratio) indicate that use of acoustic mixing to mill the APC unexpectedly provides nano-suspensions having properties and stability not available when employing high-shear mechanical milling to provide a nano-suspension.

Example 4

Preparation of Nano-Suspensions of "Test APC A" Using Acoustic Mixing (4.0 mL Scale)

The slurry composition of example A-2 was prepared on a larger scale. Thus, into a 4 mL glass vial was placed 9.12 g of yttria-stabilized zirconia milling beads and 42.6 mg of "Test Drug A", followed by 216.6 µL of a 5% aqueous solution of polymer, 45.6 µL of a 1% aqueous solution of surfactant and 1.448 mL of water. The admixture was lightly stirred manually with a spatula and the vial was sealed. The vial was placed into the acoustic mixer (Resodyne® LabRAM®), and the mixer was operated at 60 Hertz, 40% power for 90 minutes. The resulting nano-suspension was separated from the milling media using a syringe equipped with a 20-gauge needle. Particle size analysis on the recovered nano-suspension in accordance with the above-referenced procedure indicates $D_{50}$ value of 252 nm, substantially the same as the nano-suspension prepared on the 35 µL scale in Example 3.

Example 5

Simultaneous Preparation of Multiple Nano-Suspension Specimens Using a Single Acoustic Mixing Apparatus (0.35-mL Scale)

Each individual well of a plastic 96-well microtiter plate was charged with 2 mg of Naproxen, 10 µL of a 5 wt. % aqueous polymer prepared as described above, 136 µL water and 2 µL of 1 wt. % aqueous surfactant solution (prepared by dissolving 10 mg of the surfactant in 990 µL of water). Thus charged, the microtiter plate was thermally sealed and clamped into a Resodyn™ Labram™ acoustic mixer. As reflected in the table below (Table IV), the acoustic mixer was operated for a period of 90 minutes at 60 Hertz, 40% power, then removed from the well using a syringe and the resulting nano-suspension was evaluated for particle size in accordance with the foregoing described procedure. The results are reported in Table V, below.

TABLE V

| No. | Polymer | Surfactant | Particle Diameter $D_{50}$ nm/$D_{90}$ nm |
|---|---|---|---|
| B-1 | Pluronic F127 | None | 382 nm/640 nm |
| B-2 | PVP K29-32 | SDS | 240 nm/404 nm |
| B-3 | Tween80 ® | None | 310 nm/636 nm |
| B-4 | HPC-SL | SDS | 260 nm/406 nm |
| B-5 | HPMC | SDS | 228 nm/432 nm |

In a separate run, the B-2 slurry formulation was prepared as in the previous run and placed in each well of a 96 well micro-titer-plate. The plate was sealed and processed in accordance with the previous Example 5, B-2 run. At the end of 90 minutes of acoustic milling, wells were sampled randomly across each dimension of the well plate for a given mixture and each sample was evaluated for particle size. The results of this analysis are reported in Table VI for a sampling of nano-suspensions reported in Table V for Example B-2. As shown by the data of Table VI, random sampling of nano-suspensions thus prepared indicates substantially the same properties for each sample. These data indicate that acoustic mixing provides reproducible results when slurries of the same composition are milled simultaneously using this technique. It will be appreciated that these data indicate that the inventive process for the preparation of nano-suspensions can be adapted to simultaneous preparation of multiple samples where the samples comprise different slurry compositions, thereby permitting comparison of various formulations.

TABLE VI

| 1.3 wt. % Naproxen/PVP K29-32/SDS in water media | |
|---|---|
| Well Position in B-2 nano-suspension microtiter plate | Particle Diameter $D_{50}$ nm |
| (top left) | 240 nm |
| (top right) | 248 nm |

TABLE VI-continued 1.3 wt. % Naproxen/PVP K29-32/SDS in water media

| Well Position in B-2 nano-suspension microtiter plate | Particle Diameter $D_{50}$ nm |
|---|---|
| (bottom left) | 248 nm |
| (bottom right) | 254 nm |
| (middle left) | 248 nm |
| (middle right) | 252 nm |

Example 6

Scale-Up of Formula 2B, Example 4—Acoustic Mixing Apparatus (140-mL Scale)

The nano-suspension of Formulation B-2 prepared on the 0.35 mL scale in Example 5 was prepared at a 140 mL scale. Accordingly, into a 140-mL plastic bottle was placed 15.33 g of Naproxen, 12.78 mL of a 30 wt. % aqueous solution of PVP K29-32, 2.94 mL of a 5 wt. % aqueous solution of SDS and 30.27 mL of water, and 319.2 g of yttria-stabilized zirconia milling beads (Tosoh YTZ). The bottle was capped and inserted into the acoustic mixing apparatus and the contents were mixed at 40% power for 90 minutes. At the end of 90 minutes the resultant slurry was separated from the milling media and by a syringe equipped with a 20-gauge needle and the recovered nano-suspension was evaluated for particle size and agglomeration. In the samples obtained, 81% of the drug charged into the slurry was found to be present in the nano-suspension (81% yield). The particle size analysis confirmed that the nano-suspension prepared at this scale was the same as the nano-suspension prepared from the B-2 slurry composition used in the microtiter plate preparation of Example 4. These data indicate that nano-suspensions prepared using similar resonate acoustic conditions permit scale-up in container volume and drug concentration (as in this example, from a 2 mg Naproxen in 0.35 mL container to 15.33 g Naproxen in 140 mL container (approximately 7600× scale increase) without significant re-engineering of equipment or procedural changes to provide substantially the same results obtained using bench-scale or micro-scale preparation. Accordingly, it will be appreciated that the process of the present invention facilitates transition of formulations from "screening" level scale to commercial scale with little re-engineering of the process required.

Example 7

Figure 1:
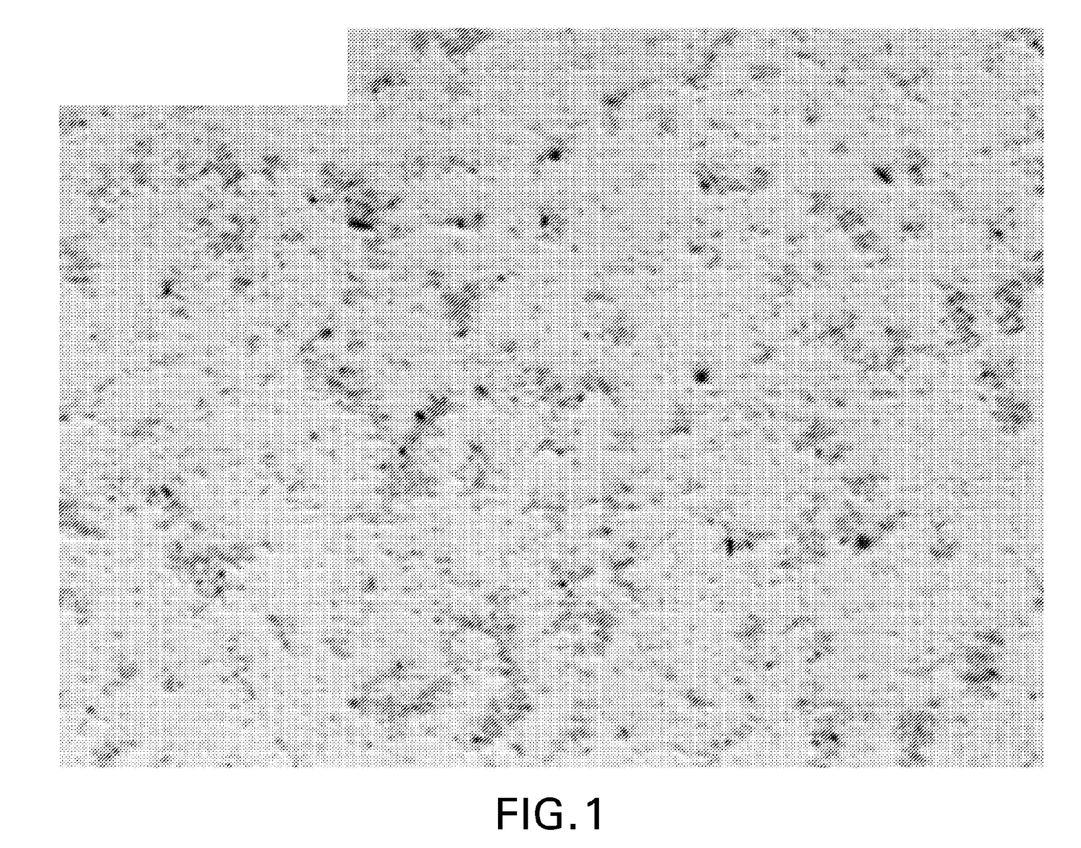
FIG. 1 presents a photomicrograph of a nano-suspension comprising Test drug "B" and PVPK29-32, prepared using a high-shear mechanical milling apparatus, 60 minutes milling time.
Figure 2:
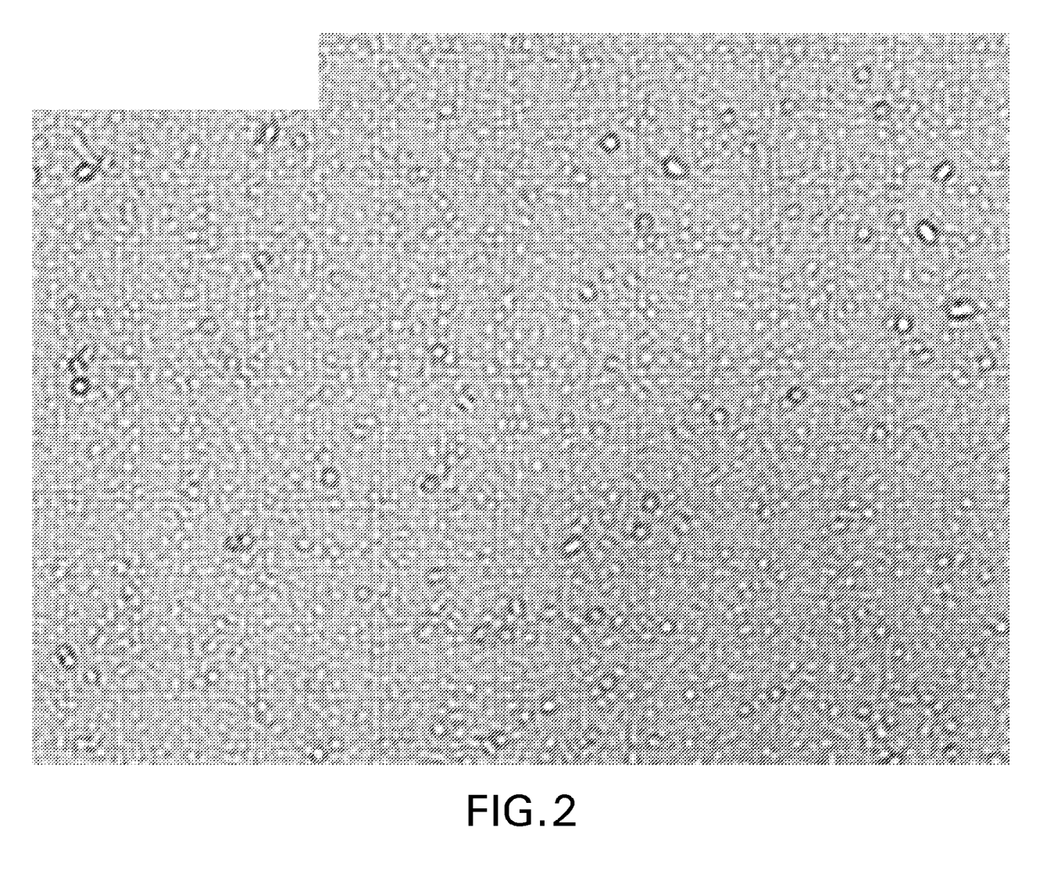
FIG. 2 presents a photomicrograph of a nano-suspension comprising Test drug "B" and PVPK29-32, prepared using an acoustic mixer as a milling apparatus, 90 minutes milling time.

Observed Agglomeration in Nano-Suspension Specimens: Comparison of Samples Prepared Using Acoustic Mixing and Mechanical Shear Apparatus With reference to Tables III (Comparative Example 2) and IV (Example 3), above, comparison of the $D_{50}$ and $D_{90}$ values reported in the tables indicates that significant agglomeration occurs in suspensions prepared using high-shear milling process that is not observed when acoustic mixing is employed to mill the APC. The surprising difference in properties of the suspensions produced using high-shear milling and the acoustic milling process of the invention are further illustrated with reference to FIG. 1, which is a micrograph of a nano-suspension prepared in accordance with Sample S-2 (slurry comprising active pharmaceutical compound "Test APC A" and an aqueous dispersion medium comprising polymer PVP K29-32), after 60 minutes of high-shear milling, and FIG. 2, which is a micrograph of a nano-suspension prepared in accordance with Sample A-2 (slurry comprising active pharmaceutical compound "Test APC A" and an aqueous dispersion medium comprising polymer PVP K29-32) after 90 minutes of acoustic milling. These photomicrographs indicate that the sample prepared with high-shear milling exhibits extensive agglomeration after only 60 minutes of milling, while the sample prepared using an acoustic milling did not display visible agglomeration even after 90 minutes of milling. These data indicate that the process of the invention provides nanoparticles which are less surface active than nanoparticles provided by processes which employ high-shear mixing. As will be appreciated, the lower agglomeration present in nano-suspensions of the present invention illustrates the lower surface activity of the nanoparticles provided by the inventive process.

Example 8

Figure 3:
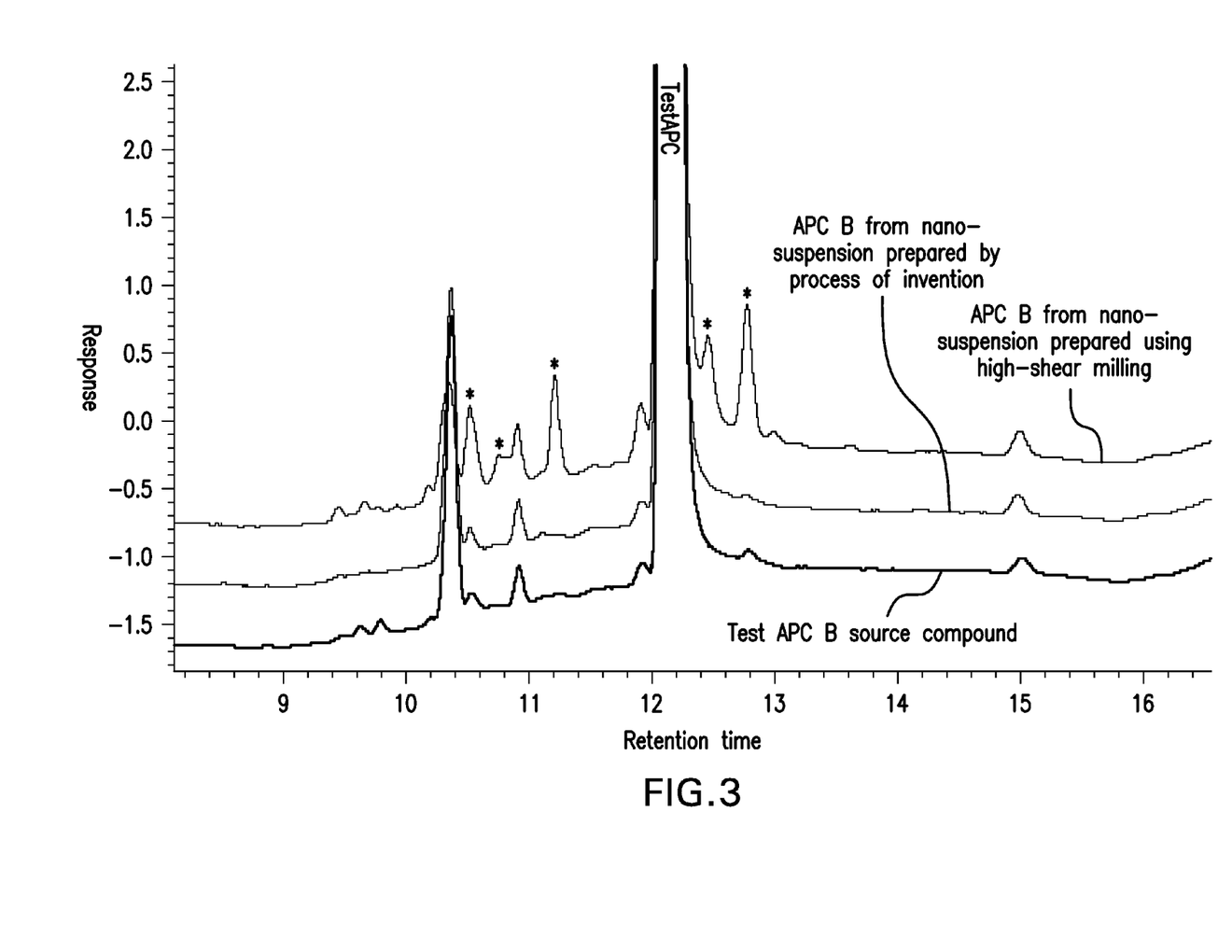
FIG. 3 presents a stacked chromatogram showing high performance liquid chromatography analysis comparing: (i) "Test APC B" as sourced, the active pharmaceutical compound used in the examples (bottom trace); (ii) the "Test APC B" compound present in a nano-suspension prepared by a process of the present invention (middle trace); and (iii) "Test APC B" present in a nano-suspensions prepared using high shear milling conditions (top trace).

HPLC Analysis of Nano-Suspensions Prepared by Acoustic Mixing and Mechanical Shear Apparatus With reference to FIG. 3, the APC present in a nano-suspension of the invention and in a nano-suspension prepared using a high-shear milling process is compared by HPLC analysis with the powdered APC employed in preparing the slurries employed in providing each of these nano-suspensions. Accordingly, the top trace in FIG. 3 presents HPLC analysis of the APC isolated from a nano-suspension comprising "Test APC B" and an aqueous dispersion medium comprising HPC-SL polymer and SDS surfactant which was prepared by a high-shear milling process in accordance with Comparative Example 2. The middle trace in FIG. 3 presents HPLC analysis of the APC isolated from a nano-suspension prepared from the same slurry constituents used in preparing the nano-suspension of the top trace ("Test APC B", HPC-SL polymer/SDS surfactant), but acoustic milling was employed in accordance with Example 3, to prepare the nano-suspension analyzed in the middle trace. The bottom trace in FIG. 3 presents HPLC analysis of a sample of the "Test APC B" which was employed in preparing the slurries from which the Example and Comparative Example nano-suspensions subjected to HPLC analysis were prepared.

With reference to FIG. 3, when the peak for drug product is normalized, the chromatographs indicate that impurities, most likely degradation products, are present in the APC of the nano-suspension prepared using high-shear milling that were either not present in the nano-suspension prepared using acoustic milling or are present in the nano-suspension prepared using acoustic milling at about the same level that these impurities were present in the "Test Drug B" APC sample (see for example the peaks growing in on either side of the drug-product peak located at retention time 12.12 and the major impurity present at retention time 10.34 in the top trace). These data indicate that the acoustic milling process of the invention unexpectedly provides less degradation of the APC when preparing a nano-suspension than is available using a high-shear milling processes.

Example 9

Preparation of Nano-Suspensions Containing High Drug Loads Prepared by Acoustic Mixing Nano-suspensions comprising "Test APC C" (a class IV drug) were prepared both by high-shear milling and acoustic-milling the using slurries prepared with the same relative weights, as shown for each entry of Table VII. The difference in volume of slurry prepared accounts for the difference in volume of the mixing chamber of the Nanomill® apparatus and the vial utilized with the acoustic mixer apparatus, providing the same ratio of APC and suspending medium in the slurry used in each process.

TABLE VII

| Constituent | Weight charged Nanomill ® 10 mL milling chamber | Weight Charged into 4 mL glass vial (Acoustic Mixer) |
|---|---|---|
| "Test APC C" | 233 mg | 88 mg |
| Milling media | 5.43 g polystyrene milling beads (Elan Drug Technologies) | 9.12 g yttria-stabilized zirconia milling beads (Tosoh YTZ(R) grinding media) |
| Aqueous 5% PVP-K15-17 polymer dispersion medium | 0.140 g | 0.053 g |
| Aqueous 5% DCA surfactant | 0.034 g | 0.013 g |
| Water | 4.254 g | 1.597 g |

Each milling operation was carried out for 90 minutes, and the resultant products were recovered using either centrifugation (high-shear milling process) or a syringe fitted with a 20 gage needle (acoustic milling process). The materials recovered were subjected to particle size analysis in accordance with the procedure referenced herein, and the results are reported in Table VIII, below.

TABLE VIII

| Property | Elan Nanomill ® | Resodyn LabRAM |
|---|---|---|
| Nanoparticle Drug Loading | 96% | 96% |
| Drug particle diameter ($D_{50}$) | >3000 nm | 280 nm |

This example demonstrates that the acoustic milling process of the present invention can be used to prepare a stable nano-suspension using an APC/surface-active constituent ratio that provides a nanoparticle having a 96% drug load. In contrast, that ratio of APC/surface-active constituent utilized in the slurry does not provide a nano-suspension when a high-shear milling process is employed. These data illustrate that the process of the present invention provides nano-suspensions which are of fundamentally different character than those provided using high-shear mechanical milling. Moreover, the nano-suspensions of the present invention which are provided by the process of the present invention are clearly distinguished in their properties from nano-suspensions provided by high-shear milling processes.

What is claimed is:

1. A method of preparing a nano-suspension, the method comprising applying low frequency acoustic energy at a frequency of 60 Hertz to an admixture comprising: (i) an active pharmaceutical compound; (ii) an aqueous dispersion medium which includes a surface-active polymer and optionally includes a surfactant as a stabilizer; and (iii) milling media, wherein said acoustic energy is applied until said active pharmaceutical compound has been milled to the desired average diameter in the nanoparticle range.

2. The method of claim 1, wherein the acoustic energy is applied as a standing wave.

3. The method of claim 2 wherein the acoustic energy imparts a force of from about 10 G to about 100 G.

4. A nano-suspension prepared in accordance with the method of claim 3.

5. The nano-suspension of claim 4 wherein said nanoparticles comprise in excess of 75-99 wt % active pharmaceutical compound.

6. A process for preparing multiple nano-suspension samples simultaneously, the method comprising: (a) preparing in each chamber in a multi-chambered apparatus, an admixture comprising: (i) an active pharmaceutical compound; (ii) an aqueous dispersion medium; and (iii) a milling media; and (b) applying low frequency acoustic energy at a frequency of 60 Hertz to said multi-chambered apparatus until said drug particles have acquired the desired average diameter in the nanoparticle range.

7. The process of claim 6 wherein the acoustic energy is applied as a standing wave.

8. The process of claim 7 wherein the acoustic energy imparts a force of from about 10 G to about 100 G.

9. The method of claim 1 wherein the acoustic energy imparts a force of from about 10 G to about 100 G.

10. A nano-suspension prepared in accordance with the method of claim 1.

11. A nano-suspension prepared in accordance with the method of claim 2.

12. A nano-suspension prepared in accordance with the method of claim 3.

13. The process of claim 6 wherein the acoustic energy is applied as a standing wave.

14. The process of claim 6 wherein the acoustic energy imparts a force of from about 10 G to about 100 G.

* * * * *